US011229915B2

(12) United States Patent
Manford et al.

(10) Patent No.: US 11,229,915 B2
(45) Date of Patent: Jan. 25, 2022

(54) JET MILLING METHOD

(71) Applicant: VECTURA LIMITED, Chippenham (GB)

(72) Inventors: Fergus Manford, Chippenham (GB); Matthew Green, Chippenham (GB)

(73) Assignee: VECTURA LIMITED, Chippenham (GB)

( * ) Notice: Subject to any disclaimer, the term of this patent is extended or adjusted under 35 U.S.C. 154(b) by 747 days.

(21) Appl. No.: 15/758,642

(22) PCT Filed: Sep. 9, 2016

(86) PCT No.: PCT/EP2016/071321
§ 371 (c)(1),
(2) Date: Mar. 8, 2018

(87) PCT Pub. No.: WO2017/042341
PCT Pub. Date: Mar. 16, 2017

(65) Prior Publication Data

US 2018/0257084 A1 Sep. 13, 2018

(30) Foreign Application Priority Data

Sep. 9, 2015 (EP) .................................... 15184551

(51) Int. Cl.

| | |
|---|---|
| *B02C 19/06* | (2006.01) |
| *A61K 9/14* | (2006.01) |
| *A61K 31/40* | (2006.01) |
| *B02C 23/18* | (2006.01) |

(52) U.S. Cl.
CPC ............ *B02C 19/061* (2013.01); *A61K 9/145* (2013.01); *A61K 31/40* (2013.01); *B02C 19/06* (2013.01); *B02C 23/18* (2013.01)

(58) Field of Classification Search
CPC ............................................. B29B 2017/0428
See application file for complete search history.

(56) References Cited

U.S. PATENT DOCUMENTS

| | | | | |
|---|---|---|---|---|
| 5,637,620 A * | 6/1997 | Trofast | A61K 9/145 514/630 |
| 5,716,751 A * | 2/1998 | Bertrand | B02C 19/068 241/15 |
| 5,992,773 A | 11/1999 | Schwechten | |
| 6,641,063 B2 | 11/2003 | Vemuri et al. | |

(Continued)

FOREIGN PATENT DOCUMENTS

| | | |
|---|---|---|
| EP | 2218509 | 8/2010 |
| JP | 2007217765 | 8/2007 |

(Continued)

OTHER PUBLICATIONS

SonoTek—How Ultrasonic Nozzles Work (Year: 2012).*
(Continued)

*Primary Examiner* — Faye Francis
(74) *Attorney, Agent, or Firm* — Barnes & Thornburg LLP; Ryan P. Cox

(57) ABSTRACT

Systems and methods are disclosed for simultaneously jet milling and conditioning particulate material comprising a grinding chamber and an aerosol generator arranged to supply liquid aerosol into the grinding chamber. A composition made by this method is also disclosed.

17 Claims, 4 Drawing Sheets

(56) References Cited

U.S. PATENT DOCUMENTS

| | | |
|---|---|---|
| 7,789,331 B2 | 9/2010 | Zehavi et al. |
| 7,850,105 B2 * | 12/2010 | Ito ........................ B02C 19/061 |
| | | 241/39 |
| 8,235,314 B2 | 8/2012 | Lee |
| 9,010,666 B2 | 4/2015 | Nied et al. |
| 2003/0230652 A1 | 12/2003 | Lortz et al. |
| 2004/0118007 A1 | 6/2004 | Chickering et al. |
| 2006/0127573 A1 * | 6/2006 | Hauk ...................... B01J 2/006 |
| | | 427/212 |
| 2006/0257491 A1 | 11/2006 | Morton et al. |
| 2008/0051473 A1 | 2/2008 | Lortz et al. |
| 2009/0269412 A1 | 10/2009 | Morton et al. |
| 2011/0073689 A1 * | 3/2011 | Paulat .................... C09C 3/041 |
| | | 241/15 |
| 2012/0298782 A1 | 11/2012 | Nied et al. |
| 2014/0080890 A1 | 3/2014 | Snape et al. |
| 2014/0275517 A1 | 9/2014 | Kazmi et al. |
| 2015/0093440 A1 | 4/2015 | Hong et al. |

FOREIGN PATENT DOCUMENTS

| | | |
|---|---|---|
| JP | 2009154146 | 7/2009 |
| JP | 2013042814 | 3/2013 |
| WO | 1999054048 | 10/1999 |
| WO | 2000032165 | 6/2000 |
| WO | 2001000312 | 1/2001 |
| WO | 2012051426 | 4/2012 |
| WO | 2014144894 | 9/2014 |

OTHER PUBLICATIONS

Written Opinion of the International Searching Authority for PCT/EP2016/071321 dated Nov. 30, 2016.
Micronizer Jet Mill. Sturtevant, Inc., 2000.
Jet Pulverizer. The Jet Pulverizer Company, 2000.
Advances in Powder Micronization Technology for the Pharmaceutical Industry. The Journal of Pharmaceutical Processing, 2003.

* cited by examiner

JET MILLING METHOD

CROSS-REFERENCE TO RELATED APPLICATIONS

This application is a United States national stage of International Application No. PCT/EP2016/071321, filed Sep. 9, 2016, which was published as International Publication No. WO 2017/042341, and which claims benefit of European Patent Application No. 15184551.8, filed Sep. 9, 2015, the entire contents of which are hereby expressly incorporated herein by reference.

INTRODUCTION

This application relates to jet mills and jet milling methods used for the preparation and stabilization of particulate materials, preferably to systems and methods which provides physicochemical stability of the particulate materials as well as compositions incorporating such particles.

BACKGROUND

Crystalline particulate materials are generally too big to be used as supplied in many industries and often require size reduction (micronisation). Typically, unmicronised source powders will exist in particle sizes substantially greater than 10 µm, with typical distributions resembling $D_{10}>10$ µm, $D_{50}>90$, $D_{90}>250$ µm. One common method of micronizing source powders is jet milling.

The multiple high speed/high energy collisions that occur within the grinding chamber of a jet mill provide the milling action which is required to break the particles down to the appropriate size. This process, however, can result in particle characteristics with an undesired level of physiochemical instability. It is also well known that such milling action may induce the generation of non-crystalline (amorphous) material, especially on the surface of the particles where particles have collided either with each other or the side of the grinding chamber of the jet mill. Such non-crystalline material can lead to significant physicochemical instability of the resulting micronized particles resulting in particles that may fuse, aggregate, and/or agglomerate. Amorphous material may be present in the form of amorphous regions on an otherwise crystalline particle.

It has been suggested that conducting micronisation in the presence of humidified air or other gas may help to reduce the generation of amorphous materials. Both WO1999 054048 and WO2000 032165 disclose that milling crystalline particles, especially medicament powders intended for administration by inhalation under increased humidity can reduce the generation of amorphous material.

Similarly, according to U.S. Pat. No. 8,235,314 B2, it is considered advantageous to perform the micronization process with humidified gas (typically air or nitrogen) to produce the best particles in terms of size, stability and other valuable properties. U.S. Pat. No. 8,235,314 B2 in particular considered it advantageous to maximize the amount of water vapour present during the micronization process, without producing liquid condensate.

WO2014 144894 discloses methods and systems for the preparation of conditioned micronized active agents and in-process conditioning of micronized active agent particles and compositions comprising conditioned micronized materials. WO2014 144894 discloses a process wherein liquid droplets are heated, evaporated and then introduced into a conditioning zone after particles have been micronized in a jet mill.

However there remains a need for an improved jet mill apparatus and jet milling method for micronizing crystalline particles.

SUMMARY OF THE INVENTION

We disclose an improved jet mill and process involving jet milling with a liquid aerosol supplied directly into the grinding chamber of the jet mill to produce a stable particle as determined by Dynamic Vapour Sorption (DVS) along with imparting an excellent Particle Size Distribution (PSD) profile determined by laser diffraction as measured by $D_{10}$, $D_{50}$ and $D_{90}$ values.

Unlike the prior art which uses modified pressurised gas lines leading to the jet mill to provide humidity, the jet mill and method of the invention supply a liquid aerosol directly into the grinding chamber thereby avoiding the need for heat or having to modify or contaminate these pressurised gas feed lines.

Furthermore, supplying the liquid aerosol directly into the grinding chamber of the jet mill allows for real time modification of the processing parameters and in particular allows liquid aerosol to be introduced under conditions that are less likely to denature the particulate material, such as ambient temperature and humidity.

The jet mill and method of the invention also allows additional components to be used in the solution from which the liquid aerosol is formed. This is introduced into the grinding chamber at the point of micronisation which avoids contaminating the pressurised gas lines leading to the jet mill.

DETAILED DESCRIPTION OF INVENTION

Systems and methods for simultaneously milling and conditioning particulate material are described herein involving a jet mill comprising a grinding chamber and an aerosol generator arranged to supply liquid aerosol into the grinding chamber.

In one embodiment a jet mill comprising an integrated aerosol generator arranged to supply liquid aerosol into the grinding chamber of the jet mill is disclosed.

In one embodiment, the systems and methods described herein involve a jet mill wherein the aerosol generator which is external to the grinding chamber and the external aerosol generator is configured with a port to supply liquid aerosol into the grinding chamber.

In one embodiment, the systems and methods described herein involve a jet mill wherein the port is arranged to simultaneously supply a grinding material and liquid aerosol as a feed stock into the grinding chamber.

In one embodiment, the systems and methods described herein involve a jet mill wherein the port is arranged to simultaneously supply a co-located grinding material and liquid aerosol as a feed stock into the grinding chamber.

In one embodiment, the systems and methods described herein involve a jet mill wherein the jet mill is a spiral jet mill, a fluidized bed jet mill, an opposed fluid jet mill or a high density bed jet mill.

In one embodiment, the systems and methods described herein involve a jet mill wherein the aerosol generator comprises a nebuliser, preferably wherein the nebuliser is a vibrating mesh, jet nebulizer or an ultrasonic wave nebulizer.

In one embodiment, the systems and methods described herein involve a jet mill wherein the aerosol generator produces a condensed vapour.

In one embodiment, the systems and methods described herein involve a jet mill wherein the aerosol generator comprises a spray drying atomiser, a two-fluid nozzle atomiser or a centrifugal atomiser.

In one embodiment, the systems and methods described herein involve a jet mill further comprising a powder feeder wherein the powder feeder comprises a rotary valve, a vibratory tray or a screw feeder, preferably wherein the powder feed rates ranges from 10 g/hour to production mill rates of up to 900 kg/hr.

In one embodiment, the systems and methods described herein involve a jet mill wherein the aerosol generator produces liquid aerosol with a $D_{90}$ less 100 µm, preferably less 50 µm or more preferably less 20 µm prior to entering the grinding chamber as measured by laser diffraction.

In one embodiment, the systems and methods described herein involve a jet mill, wherein the aerosol generator produces liquid aerosol which has a temperature less than 100° C. upon entering the grinding chamber.

In one embodiment, the systems and methods described herein involve a jet mill wherein the aerosol generator produces a liquid aerosol at atmospheric pressure.

In one embodiment, the systems and methods described herein involve a jet mill wherein the liquid aerosol is combined with a grinding material at atmospheric pressure.

In one embodiment, the systems and methods described herein involve a jet mill comprising a vortex modifier for altering the residence times of a feed stock in the grinding chamber, wherein the feed stock comprises a grinding material and liquid aerosol.

In one embodiment, the methods described herein involve a process of producing micronized material, the method comprising jet milling a feed stock comprising a grinding material and liquid aerosol.

In one embodiment, the methods described herein involve a process wherein the grinding material comprises particulate material, optionally unmicronised particulate material.

In one embodiment, the methods described herein involve a process wherein the grinding material comprises a pharmaceutically active material.

In one embodiment, the methods described herein involve a process wherein the pharmaceutically active material, comprises a β2-agonist, a steroid, an anticholinergic, a phosphodiesterase-4-inhibitor, an Ata agonist, an IL-13 inhibitor or a calcium blocker.

In one embodiment, the methods described herein involve a process wherein the $\beta_2$-agonist is selected from albuterol (salbutamol), preferably albuterol sulfate; carmoterol, preferably carmoterol hydrochloride; fenoterol; formoterol; milveterol, preferably milveterol hydrochloride (GSK159797); metaproterenol, preferably metaproterenol sulfate; olodaterol; procaterol; salmeterol, preferably salmeterol xinafoate; TA-2005; terbutaline, preferably terbutaline sulphate; vilanterol, preferably vilanterol trifenatate or indacaterol, preferably indacaterol maleate In one embodiment, the methods described herein involve a process wherein the steroid is selected from budesonide; beclamethasone, preferably beclomethasone dipropionate; ciclesonide; fluticasone, preferably fluticasone furoate; GSK233705 or mometasone, preferably mometasone furoate. In one embodiment, the methods described herein involve a process wherein the anticholinergic is selected from aclidinium, preferably aclidinium bromide; glycopyrronium, preferably glycopyrronium bromide; ipratropium, preferably ipratropium bromide; oxitropium, preferably oxitropium bromide; tiotropium, preferably tiotropium bromide; umeclidinium, preferably umeclidinium bromide; CHF 4226 (Chiesi) and SVT-40776.

In one embodiment, the methods described herein involve a process wherein the grinding material comprises a pharmaceutical additive.

In one embodiment, the methods described herein involve a process wherein the pharmaceutically active material is co-milled with the pharmaceutical additive.

In one embodiment, the methods described herein involve a process wherein the pharmaceutical additive is in an amount of from 1 to 25% (w/w), more preferably from 2 to 20% (w/w), more preferably 3 to 15% (w/w), more preferably 4 to 10% (w/w) but most preferably from 5 to 7.5% (w/w) of the co-jet milled combination of the pharmaceutically active material and pharmaceutical excipient.

In one embodiment, the methods described herein involve a process wherein the pharmaceutical additive is selected from a metal stearate, sodium lauryl sulphate, sodium stearyl fumarate, sodium stearyl lactylate, preferably calcium stearate, lithium stearate, magnesium stearate, sodium stearate, zinc stearate, stearyl alcohol or sodium benzoate preferably, preferably the additive material comprises magnesium stearate.

In one embodiment, the methods described herein involve a process wherein the grinding material comprises a pharmaceutical excipient.

In one embodiment, the methods described herein involve a process wherein the pharmaceutical excipient comprises lactose, mannitol, glucose, trehalose, cellobiose, sorbitol or maltitol.

In one embodiment, the methods described herein involve a process wherein the micronized pharmaceutically active material is subsequently blended with a pharmaceutical excipient preferably wherein the pharmaceutical excipient is a carrier, preferably lactose, more preferably anhydrous lactose, more preferably alpha-lactose monohydrate.

In one embodiment, the methods described herein involve a process wherein the liquid aerosol has a $D_{90}$ less 100 µm, preferably less 50 µm or more preferably less 20 µm as measured by laser diffraction.

In one embodiment, the methods described herein involve a process wherein the liquid aerosol is an organic liquid.

In one embodiment, the methods described herein involve a process wherein the organic liquid aerosol is polar, preferably wherein the liquid aerosol comprises water.

In one embodiment, the methods described herein involve a process wherein the organic liquid aerosol is or non-polar.

In one embodiment, the methods described herein involve a process wherein the liquid aerosol is a non-organic liquid.

In one embodiment, the methods described herein involve a process wherein the non-organic liquid aerosol is polar or non-polar.

In one embodiment, the methods described herein involve a process wherein the liquid aerosol imparts a milling humidity in the grinding chamber of more than 20% RH, preferably more than 30% RH, preferably more than 40% RH, preferably more than 50% RH or more preferably 60% RH as measured by a hygrometer.

In one embodiment, the methods described herein involve a process wherein the liquid aerosol is produced at atmospheric pressure.

In one embodiment, the methods described herein involve a process wherein the liquid aerosol is combined with the grinding material at atmospheric pressure.

In one embodiment, the methods described herein involve a process wherein the jet mill uses a milling gas selected from air, steam, hydrogen, helium, nitrogen, carbon dioxide or combination thereof.

In one embodiment, the methods described herein involve a process wherein the grinding material comprises a liquid.

In one embodiment, the methods described herein involve a process wherein the liquid aerosol comprises a pharmaceutically active material.

In one embodiment, the methods described herein involve a process wherein the liquid aerosol comprises a pharmaceutical additive.

In one embodiment, the methods described herein involve a process wherein the liquid aerosol comprises a pharmaceutical excipient.

In one embodiment, the methods described herein involve a process wherein the milling step occurs at a temperature in the range from 0° C. to 100° C., preferably 10° C. to 90° C., more preferably 20° C. to 80° C.

In one embodiment, the methods described herein involve a process wherein the jet milling is carried out at an averaged powder feed rate of between 0.1 and 50 g/min, preferably at a feed rate of between 0.5 and 40 g/min, preferably at a feed rate of between 1 and 30 g/min, preferably at a feed rate of between 1.5 and 25 g/min, preferably at a feed rate of between 0.1 and 20 g/min, preferably at a feed rate of between 0.5 and 15 g/min, preferably at a feed rate of between 1 and 10 g/min, preferably at a feed rate of between 1.5 and 5 g/min.

In one embodiment, the methods described herein involve a process wherein the jet milling is carried out at a grinding pressure of more than 2 bar below an inlet pressure.

In one embodiment, the methods described herein involve a process wherein the jet milling is carried out at an inlet pressure of between 3 and 12 bar, preferably at an inlet pressure of between 4 and 10 bar, or more preferably at an inlet pressure of between 5 and 9 bar.

In one embodiment, the methods described herein involve a process wherein the grinding pressure is carried out at between 1 and 10 bar, preferably at a pressure of between 2 and 8 bar, or more preferably at a pressure of between 3 and 7 bar.

In one embodiment, the methods described herein involve a process for reducing the presence of amorphous material on the surface of a micronized pharmaceutically active material comprising combining the pharmaceutically active material and a liquid aerosol as a feed stock in a grinding chamber and jet milling the feed stock.

In one embodiment, the methods described herein involve a process wherein the pharmaceutically active material is selected from glycopyrrolate, indacaterol or mometasone.

In one embodiment, the methods described herein involve a process wherein the micronized pharmaceutically active material particles contain less than 5% (w/w), less than 4% (w/w), less than 3% (w/w), less than 2% (w/w), preferably less than 1% (w/w) amorphous material immediately after milling as measured by dynamic vapour sorption.

In one embodiment, a formulation made by a method is described, wherein the micronized pharmaceutically active material particles contain less than 5% (w/w), less than 4% (w/w), less than 3% (w/w), less than 2% (w/w), preferably less than 1% (w/w) amorphous material immediately after milling as measured by dynamic vapour sorption.

In one embodiment, the methods described herein involve a process wherein jet milling unmicronised pharmaceutically active material with a liquid aerosol increases the relative humidity (RH) of the milling gas to greater than 20% RH, preferably greater than 25% RH, preferably greater than 30% RH, preferably greater than 35% RH, more preferably greater than 40% RH for the duration of the jet milling process.

In one embodiment, the methods described herein involve jet milling particulate material with a liquid aerosol that increases the relative humidity (RH) of the milling gas to greater than 1% RH, preferably greater than 2% RH, preferably greater than 3% RH, preferably greater than 4% RH, preferably greater than 5% RH, preferably greater than 10% RH, more preferably greater than 15% RH for at least a portion of the duration of the jet milling process. Preferably wherein the particulate material comprises a pharmaceutically active material. Preferably wherein the particulate material comprises a combination of a pharmaceutically active material and a pharmaceutical additive, and optionally a pharmaceutical excipient as required.

In one embodiment, the methods described herein involve jet milling particulate material with a liquid aerosol that increases the relative humidity (RH) of the milling gas to between 1% RH and 20% RH, preferably between 2% RH and 19% RH, preferably between 3% RH and 18% RH, preferably between 4% RH and 17% RH, preferably between 5% RH and 16% RH, preferably between 6% RH and 15% RH, more preferably between 5% RH and 20% RH for at least a portion of the duration of the jet milling process. Preferably wherein the particulate material comprises a pharmaceutically active material. Preferably wherein the particulate material comprises a combination of a pharmaceutically active material and a pharmaceutical additive, and optionally a pharmaceutical excipient as required.

In one embodiment, the methods described herein involve jet milling particulate material with a liquid aerosol, the liquid aerosol being at least a partial solvent of the particulate material. Preferably wherein the particulate material comprises a pharmaceutically active material. Preferably wherein the particulate material comprises a combination of a pharmaceutically active material and a pharmaceutical additive, and optionally a pharmaceutical excipient as required.

In one embodiment, a formulation made by a method is described, for use in treatment of a respiratory condition, wherein the respiratory condition is chronic obstructive pulmonary disease (COPD), asthma, cystic fibrosis (CF) or related airway diseases.

FIGURES

DESCRIPTION OF THE JET MILL

The jet mill of the invention is not limited to the illustrated embodiments.

The improved jet mill comprises a milling apparatus in which a feed stock, comprising a grinding material and liquid aerosol, is entrained in a flow of gas causing the entrained feed stock to repeatedly collide with itself and cause size reduction of the grinding material. For example, the feed stock may comprise particles of pharmaceutically active material. A circulating gas flow, such as the described vortex below, increases the interaction length for collisions between the constituent parts of the feed stock. The feed stock, comprising a grinding material and liquid aerosol, need not be entrained in a separate gas flow and could be introduced under gravity into the milling chamber.

Figure 1:
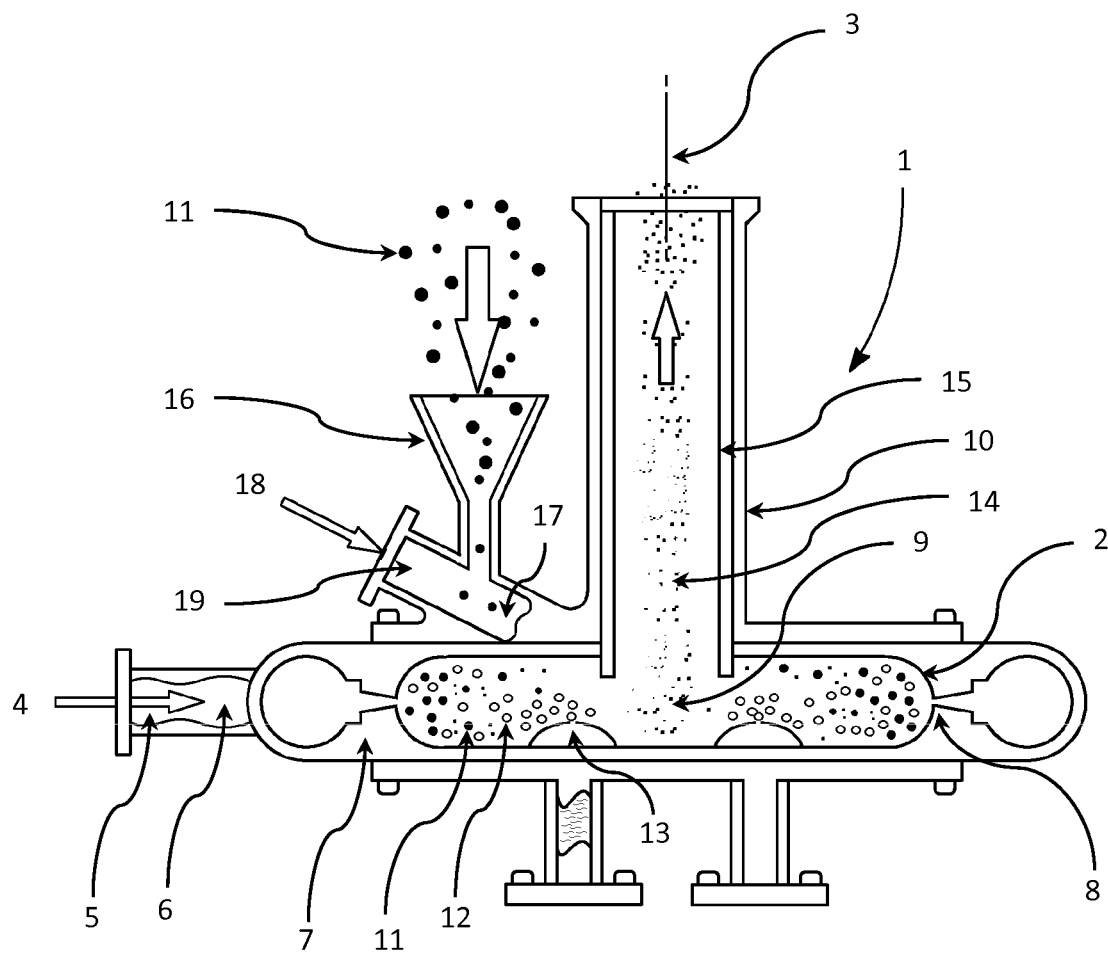
FIG. 1 is a partially sectioned view of a jet mill with an internal aerosol generator arranged to supply liquid aerosol into the grinding chamber of the jet mill.
Figure 2:
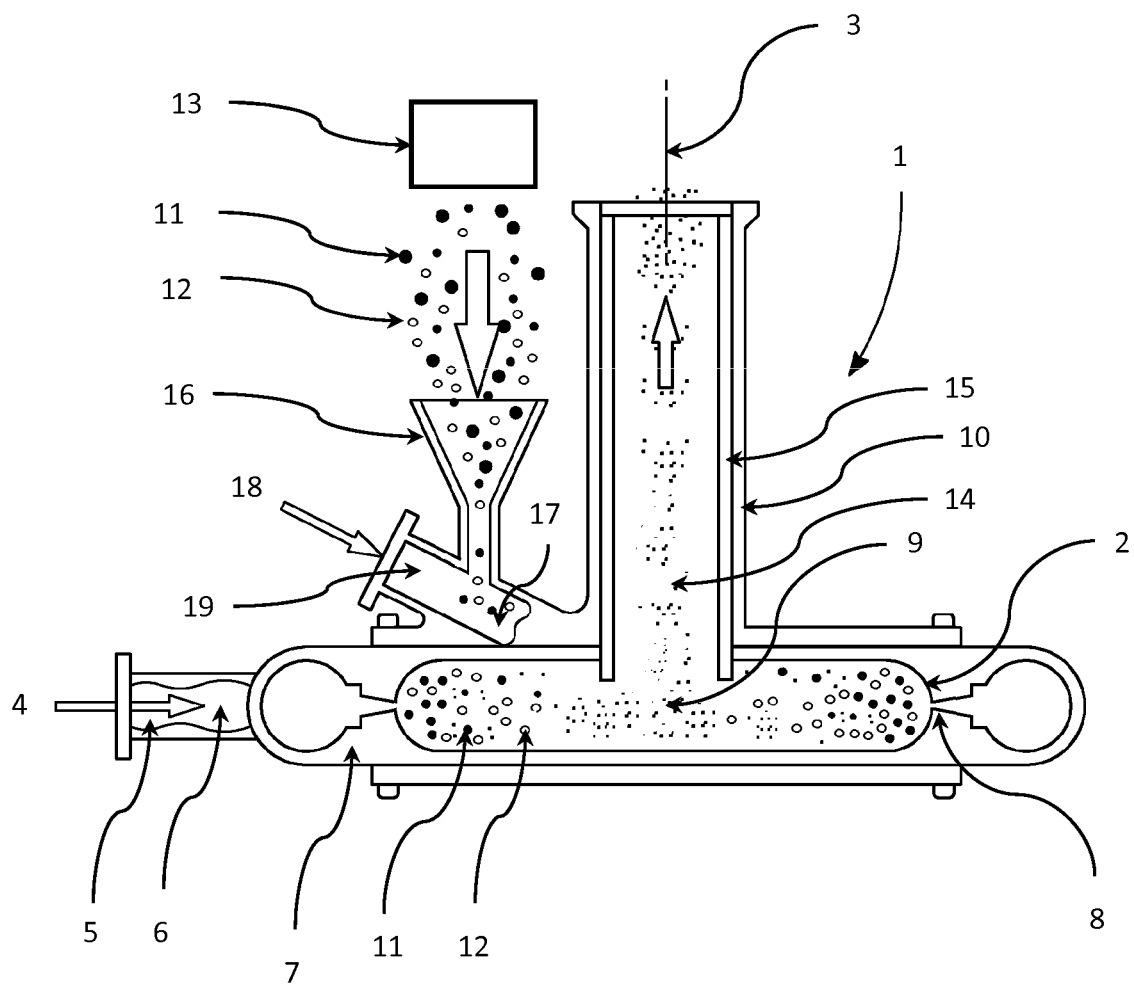
FIG. 2 is a partially sectioned view of a jet mill with an external aerosol generator arranged to supply liquid aerosol into the grinding chamber of the jet mill.

A jet mill 1 according to the invention is illustrated in the partially sectioned view of FIG. 1 or FIG. 2.

A substantially cylindrical milling chamber 2 is arranged around a central axis 3 extending vertically in the illustrated embodiment.

Compressed mill gas 4 is supplied through a gas intake 5 to a gas manifold 6 between the mill body 7 and the milling chamber 2. A plurality of jet holes 8 transfer the compressed mill gas 4 into the outer periphery of the milling chamber 2. The jet holes 8 are all aligned to set up a circulating gas flow pattern, in particular a vortex 9 of the mill gas 4 and other gas within the milling chamber 2. That is, the jet holes 8 are tangentially aligned to introduce compressed mill gas 4 into the milling chamber 2 to create a vortex 9 gas flow pattern. The resulting vortex 9 forms an inwardly directed spiral flow beginning near the outer periphery of the milling chamber 2 about the central axis 3 and shrinking with continuously decreasing radius until it is close to the central axis 3 and an outlet 10 arranged around the central axis 3 on one axial side of the milling chamber 2. The outlet 10, which forms an extraction hole for the vortex gases and entrained micronized particles, extends away from the milling chamber 2 along the chamber central axis 3.

The gas in the milling chamber 2 and any entrained particles 11 are combined with liquid aerosol 12 provided by an aerosol generator 13 arranged to supply liquid aerosol 12 into the grinding chamber 2.

In one configuration, a plurality of aerosol generators 13 may be arranged within the grinding chamber 2. In one configuration, the aerosol generator 13 may be positioned towards the periphery of the milling chamber 2. In one configuration, the aerosol generator 13 may be positioned towards the central axis 3 of the milling chamber 2.

In one configuration, the multiple aerosol generators 13 may supply different liquids presented as different liquid aerosols 12 into the grinding chamber 2.

In one configuration, the grinding chamber 2 envelopes an aerosol generator 13 arranged to supply liquid aerosol 12 into the grinding chamber 2.

In another configuration, an aerosol generator 13 is configured to supply liquid aerosol 12 and particles 11 into the grinding chamber 2.

The gas in the vortex 9 and any entrained micronized particles 14 are exhausted through the outlet pipe 10 away from the milling chamber 2 for collection in a suitable device such a collection bag or suitable cyclone apparatus.

In one configuration, a vortex modifier is placed adjacent to the vortex 9 within the grinding chamber 2. This configuration permits modification of the residence times of the entrained micronized particles 14 and liquid aerosol 12 within the grinding chamber 2 thereby extending the contact of the liquid aerosol 12 with the micronized particles 14, depending on the nature of the specific drug and jet milling parameters to be used.

In one configuration, a slidable vortex modifier 15 fits with the outlet pipe 10 and is moveable along the outlet pipe 10 so that the bottom of the slidable vortex modifier 15 can be placed at a selected axial position adjacent to the vortex 9 within the grinding chamber 2. This configuration permits modification of the residence times of the entrained micronized particles 14 and liquid aerosol 12 within the grinding chamber 2 thereby extending the contact of the liquid aerosol 12 with the micronized particles 14, depending on the nature of the specific drug and jet milling parameters to be used.

Particles 11 are loaded into a feed funnel 16 to feed the particles 11 into a port 17, for example a feed tube. The port is tangentially aligned to introduce particles 11 into the milling chamber 2 in the direction of the vortex 9 gas flow pattern. Compressed feed gas 18 is supplied to a feed gas inlet 19 directing the feed gas 18 toward the particles 11 falling with them through the funnel 16. The feed gas 18 entrains the particles 11 and flows into the milling chamber 2.

The port 17 may be formed in a side wall of the mill body 7 to introduce particles 11 at the outer periphery of the milling chamber 2 in the direction of the vortex 9 gas flow pattern.

In another configuration, the port 17 is arranged to simultaneously supply a grinding material, for example particles 11 and liquid aerosol 12 as a feed stock into the grinding chamber 2.

The swirling vortex 9 accelerates the particles 11 into a generally circular path within the milling chamber 2. The pulverization of the material primarily occurs from particle-to-particle impact although some particles 11 impact against the walls of the milling chamber 2. The tangential velocity of the vortex 9 generally increases towards the chamber central axis 3. Centrifugal force drives the larger particles towards the perimeter of the milling chamber 2, while finer particles are swept by the vortex 9 and move towards the chamber central axis 3, eventually exiting the milling chamber 2 through the outlet 10 together with the two gases 4 and 18.

The milling gas 4 and feed gas 18 should preferably be clean and all the connective piping and contact surfaces within the jet mill should preferably be made of stainless steel, ceramic or polymer preferably with polished gas-facing surfaces.

The Jet milling according to the invention typically involves the supply of gas, such as nitrogen, helium or air at pressures in the region of about 4 to 14 bar, typically 6 to 12 bar and the particles to be milled are entrained in the feed gas. High-purity nitrogen typically supplied from a liquid-nitrogen tank or clean air is advantageously used for both the milling 4 gas and feed gas 18.

The jet milling operation is typically conducted at standard pressure occurs at close to atmospheric pressure, and has a milling duration measured in milliseconds.

The final outlet temperature of the jet milling is typically at about room temperature (preferably between 10° C. and 35° C., more preferably between 20° C. and 26° C.). Typically, the milling gas is introduced into the mill at about room temperature, and exits the mill at about the same temperature. During the process however, the gas will change temperature significantly as it exits the supersonic nozzle (lower pressure and temperature) and is subsequently warmed by the energy released in the jet milling operation. Preferably the jet milling temperature is above 0° C.

The temperature of the liquid aerosol may also be controlled prior to and upon entering the grinding chamber of the jet mill. Immediately following fracture in the grinding chamber in the presence of the liquid aerosol, the surfaces of the particles immediately undergo a process of amorphous to crystalline reversion rather than experience a delay before this annealing can occur when processed downstream of the jet mill. This amorphous to crystalline reversion process can be significantly affected by the temperature of the liquid aerosol in the grinding chamber. In certain embodiments, the temperature of the liquid aerosol in the grinding chamber is less than 100° C. In specific embodiments, the temperature of the liquid aerosol in the grinding chamber may be selected from one of the following ranges, between about 1° C. and 80° C., between about 5° C. and 50° C., between about 10° C. and 40° C., and between about 15° C. and 35° C., preferably between about 20° C. and 30° C. or preferably between about 22° C. and 28° C., depending on the nature of the particulate material being processed.

In a specific embodiment the liquid aerosol solution permits the use of a liquid aerosol at or below 0° C. Salts such as pharmaceutically active materials will create freezing point depression. In specific embodiments, the temperature of the liquid aerosol in the grinding chamber may be selected from one of the following ranges, between about −20° C. and 100° C., between about −15° C. and 90° C., between about −10° C. and 80° C., between about −5° C. and 35° C. or between about −1° C. and 30° C.

The invention allows the inexpensive production of stable micronized powder with a narrow PSD. Furthermore, a jet mill conforming to the invention can be retrofitted with few parts on existing commercially available equipment.

Pharmaceutically Active Material

The feed stock to be used may include one or more pharmaceutically active materials anti-inflammatory, bronchodilatory, antihistamine, decongestant and anti-tussive drug substances that are suitable for administration by inhalation, for example for the treatment of a respiratory disease. Preferred pharmaceutically active materials include the following: Anticholinergics, Adenosine A2A receptor agonists, β2-agonists, Calcium blockers, IL-13 inhibitors, Phosphodiesterase-4-inhibitors, Kinase inhibitors, Steroids, CXCR2, Proteins, peptides, immunoglobulins such as Anti-IG-E, Nucleic acids in particular DNA and RNA, Small molecule inhibitors and Leukotriene B4 antagonists.

In one aspect, the pharmaceutically active material is an anticholinergic, for example, aclidinium, preferably aclidinium bromide; glycopyrronium, preferably glycopyrronium bromide; ipratropium, preferably ipratropium bromide; oxitropium, preferably oxitropium bromide; tiotropium, preferably tiotropium bromide; umeclidinium, preferably umeclidinium bromide; CHF 4226 (Chiesi) or SVT-40776. In one aspect, the method comprises jet milling glycopyrrolate in the presence of a liquid aerosol. In one aspect, the method comprises jet milling umeclidinium, preferably umeclidinium bromide in the presence of a liquid aerosol.

In one aspect, the pharmaceutically active material is a β2-agonist for example albuterol (salbutamol), preferably albuterol sulfate; carmoterol, preferably carmoterol hydrochloride; fenoterol; formoterol; milveterol, preferably milveterol hydrochloride (GSK159797); metaproterenol, preferably metaproterenol sulfate; olodaterol; procaterol; salmeterol, preferably salmeterol xinafoate; TA-2005; terbutaline, preferably terbutaline sulphate; vilanterol, preferably vilanterol trifenatate or indacaterol, preferably indacaterol maleate. In one aspect, the method comprises jet milling indacaterol, preferably indacaterol maleate in the presence of a liquid aerosol. In one aspect, the method comprises jet milling vilanterol, preferably vilanterol trifenatate in the presence of a liquid aerosol.

In one aspect, the pharmaceutically active material is selected from biological inhibitors of cytokine action, for example, lebrikizumab (Roche-Genentech), mepolizumab (GSK), brodalumab (Amgen/AstraZeneca) or tralokinumab (AstraZeneca).

In one aspect, the pharmaceutically active material is a steroid, for example budesonide; beclamethasone, preferably beclomethasone dipropionate; ciclesonide; fluticasone, preferably fluticasone furoate; GSK233705; mometasone, preferably mometasone furoate. In one aspect, the method comprises jet milling mometasone, preferably mometasone furoate in the presence of a liquid aerosol.

In one aspect, the formulation comprises glycopyrrolate formulated with indacaterol maleate, preferably for use in simultaneous or sequential administration in the treatment of an inflammatory or obstructive airways disease, optionally wherein any single formulation, or any combined formulation, comprises at least one particulate pharmaceutically acceptable carrier.

In one aspect, the formulation comprises glycopyrrolate formulated with indacaterol maleate and mometasone furoate, preferably for use in simultaneous or sequential administration in the treatment of an inflammatory or obstructive airways disease, optionally wherein any single formulation, or any combined formulation, comprises at least one particulate pharmaceutically acceptable carrier.

In a preferred embodiment, glycopyrrolate is in combination with indacaterol maleate and mometasone furoate wherein at least one of these pharmaceutically active materials has been co-jet milled with a liquid aerosol.

Pharmaceutical Additives

The feed stock may comprise an additive material, such as a force control agent. A force control agent is an additive material which reduces the cohesion between the fine particles within the powder formulation, thereby promoting deagglomeration upon dispensing of the powder from the dry powder inhaler. Suitable force control agents are disclosed in WO1996 023485 and they preferably consist of physiologically acceptable material, despite the fact that the material may not always reach the lung.

The force control agent may comprise or consist of one or more compounds selected from amino acids and derivatives thereof, and peptides and derivatives thereof, the peptides preferably having a molecular weight from 0.25 to 1000 Kda. Amino acids, peptides and derivatives of peptides are physiologically acceptable and give acceptable release or deagglomeration of the particles of active material on inhalation. Where the force control agent comprises an amino acid, it may be one or more of any of the following amino acids: leucine, isoleucine, lysine, valine, methionine, and phenylalanine. The force control agent may be a salt or a derivative of an amino acid, for example aspartame or acesulfame K. The D- and DL-forms of amino acids may also be used.

Force control agents which are particularly suitable for use in the present invention include, amino acids including leucine, lysine, arginine, histidine, cysteine and their derivatives, lecithin and phospholipids. The inclusion of these force control agents may improve the efficacy of the pharmaceutically active material for treating respiratory disorders such as COPD, asthma or CF.

Force control agents may include one or more water soluble substances. This helps absorption of the force control agent by the body if it reaches the lower lung. The force control agent may include dipolar ions, which may be zwitterions. It is also advantageous to include a spreading agent as a force control agent, to assist with the dispersal of the composition in the lungs.

Suitable spreading agents include surfactants such as known lung surfactants (e.g. ALEC, Registered Trade Mark) which comprise phospholipids, for example, mixtures of DPPC (dipalmitoyl phosphatidylcholine) and PG (phosphatidylglycerol). Other suitable surfactants include, for example, dipalmitoyl phosphatidylethanolamine (DPPE), dipalmitoyl phosphatidylinositol (DPPI).

The force control agent may include or consist of one or more surface active materials, in particular materials that are surface active in the solid state, which may be water soluble or water dispersible, for example lecithin, in particular soya lecithin, or substantially water insoluble, for example solid state fatty acids such as oleic acid, lauric acid, palmitic acid, stearic acid, erucic acid, behenic acid, or derivatives (such as esters and salts) thereof such as glyceryl behenate. Specific examples of such materials are phosphatidylcholines, phosphatidylethanolamines, phosphatidylglycerols and other examples of natural and synthetic lung surfactants; lauric acid and its salts, for example, sodium lauryl sulphate, magnesium lauryl sulphate; triglycerides such as Dynsan 118 and Cutina HR; and sugar esters in general. Alternatively, the force control agent may be cholesterol.

Other possible force control agents include sodium benzoate, hydrogenated oils which are solid at room temperature, talc, titanium dioxide, aluminium dioxide, silicon dioxide and starch. Also useful as force control agents are film-forming agents, fatty acids and their derivatives, as well as lipids and lipid-like materials.

The inclusion of an additive material in the dry powder formulation may suitably confer one or more of the following benefits: enhancing the powder's dispersability; protecting the formulation from the ingress of moisture; enhancing the speed and reproducibility of the process.

In a preferred embodiment the pharmaceutical additive is suitably located on the surface of the pharmaceutically active material after jet milling.

In a preferred embodiment the pharmaceutical additive is magnesium stearate.

Lactose fines also modify the interaction between the pharmaceutically active material and carrier particles affecting aerosol performance. In one embodiment the dry powder formulation may comprise fine lactose which is in an amount of preferably >3% (w/w), more preferably >5% (w/w) more preferably >8% (w/w) of the formulation residing in a blister or capsule or other suitable dispensing receptacle.

Co-Jet Milling

The terms "co-micronise" and "co-jet mill" are synonymous when used herein.

Preferably a pharmaceutically active material and the anti-adherent are pre-mixed to give a roughly homogeneous blend before being co-jet milled together as measured as a percentage coefficient of variation, as known in the art, of less than 25%, preferably less than 20%, more preferably less than 15%.

Co-jet milling drug with anti-adherent, further reduces the propensity of the micronised drug substance to form >10 µm aggregates/agglomerates immediately after milling. When co-jet milled, anti-adherent particles form a physically fused and proud particulate coating on the drug particles, and they create inter-particulate spaces between the particles of drug. The presence of this coating can be established by energy-dispersive X-ray spectroscopy (EDX). The presence of composite particles can be determined by aerosolising a sample from an inhaler into a Next Generation Impactor (NGI) at 60 L/min (equivalent to a 4 kPa pressure drop). Double coated carbon conductive tabs are placed directly under the air nozzles of stages 5, 6 and 7 of the NGI to capture the smaller powder particles. Double coated adhesive tabs prevent movement of the tab during the NGI assessment but are also small enough so that the overall airflow characteristics of the NGI pathway are not adversely affected. Once done, the powder-coated carbon conductive tabs can be transferred to SEM carbon specimen mounts, or similar. The sample can be viewed using SEM and EDX specifically looking for co-location of an atom that is unique to the additive and a separate atom unique to the drug particle, for example magnesium in the case of magnesium stearate and bromine in the case of glycopyrronium bromide.

In a preferred embodiment pharmaceutically active material is jet milled in a Hosokawa Alpine 100 AFG fluid bed opposed jet mill. Other suitable jet milling equipment include, for example, the MC 44 IR Chrispro® Jet-Mill or MC50, MC100, MC200, MC300 (Micromacinazione SA), Hosokawa's Alpine® AS-50, AS-100, AFG 140, AFG200, AFG280 and AFG400 jet mills.

The co-jet milling powder feed rates for a 50 mm diameter jet mill, for example a Hosakowa AS-50, should be kept low (preferably <20 g/min) to ensure an optimal coating of the pharmaceutically active material by the pharmaceutical additive. Feed rates higher than 20 g/min still achieve coating by the pharmaceutical additive but it will be suboptimal because too much powder passes through the mill to ensure sufficient energy is applied to each particle to achieve the desired coating with pharmaceutical additive. Feed rates will vary depending on the size of the mill used. Consequently, jet mills with 100 mm diameters, for example a Hosakowa AS-100 spiral jet mill, will be able to accommodate higher feed rates, typically <50 g/min. The jet milling may be carried out at an averaged powder feed rate of preferably between 0.1 and 50 g/min, preferably at a feed rate of between 0.5 and 40 g/min, preferably between 1 and 30 g/min, preferably between 1.5 and 25 g/min, preferably between 0.1 and 20 g/min, preferably between 0.5 and 15 g/min, preferably between 1 and 10 g/min, preferably between 1.5 and 5 g/min.

Preferably the pharmaceutically active material is co-jet milled with from 1 to 25% (w/w), more preferably from 2 to 20% (w/w), more preferably 3 to 15% (w/w), more preferably 4 to 10% (w/w) but most preferably from 5 to 7.5% (w/w) pharmaceutical additive.

Where necessary or useful, the pharmaceutically active material and/or pharmaceutical additive are sieved prior to co-jet milling.

Pharmaceutical Excipients

In a yet further embodiment, the feed stock comprises a pharmaceutical excipient. Dry powder formulations for inhalation in the treatment of respiratory diseases are generally formulated by mixing a micronised active pharmaceutical ingredient with coarse carrier particles to give an ordered mixture. The carrier particles make the micronised active pharmaceutical ingredient less cohesive and improve its flowability. This makes the powder easier to handle during the manufacturing process. The micronised active particles tend to adhere to the surface of the carrier particles when stored in a dry powder inhaler device but are dispersed from the surfaces of the carrier particles on inhalation into the respiratory tract to give a fine aerosol. The larger carrier particles impact on the throat due to their inertia and are mostly deposited in the oropharyngeal cavity.

One embodiment may include carrier particles which are mixed with the pharmaceutically active material that has been jet milled with liquid aerosol in a ratio of from 2000:1 to 5:1 by mass, especially from 200:1 to 20:1 by mass. The carrier particles may be composed of any pharmacologically inert material or combination of materials which is acceptable for inhalation. They are suitably composed of one or more crystalline sugars including monosaccharides, disaccharides, polysaccharides and sugar alcohols such as arabinose, glucose, fructose, ribose, mannose, sucrose, trehalose, lactose, maltose, starches, dextran, mannitol or sorbitol. An especially preferred carrier is lactose, for example lactose monohydrate or alpha lactose monohydrate or anhydrous lactose.

Preferably substantially all (by weight or volume) of the carrier particles have a diameter of 20 to 1000 µm, more preferably 50 to 500 µm, but especially 20 to 250 µm. The diameter of substantially all (by weight) of the carrier particles is suitably less than 355 µm. This provides good flow and entrainment characteristics and improved release of the active particles in the airways to increase deposition of the active particles in the lower lung.

It will be understood that throughout this specification the diameter of the particles referred to is the diameter of the particles as suitably determined by a Malvern Mastersizer or similar laser diffraction equipment.

Ambient Conditions

"Ambient conditions" as used herein are defined as 22° C.±5° C. and 40-50% RH. The terms "ambient temperature" and "ambient humidity" as used herein are defined as 22° C.±5° C. and 40-50% RH respectively.

EXAMPLES

Selected embodiments of the present invention will now be explained with reference to the examples. It will be apparent to those skilled in the art from this disclosure that the following descriptions of the embodiments are for illustration only and not for the purpose of limiting the invention as defined by the appended claims and their equivalents.

The examples below illustrate how micronised drug particles may be conditioned, in order to reduce the surface non-crystalline material present.

Particle Size Analysis (Dry Analysis)

The particle size distribution for the micronized glycopyrrolate formulations was determined by Malvern Mastersizer analysis (Malvern Mastersizer 3000, using the Aero S dry dispersion method at 4 Bar and a feed rate of between 30-40%). The optical properties used included a refractive index of 1.52 and an absorption value of 1.0.

Particle Size Analysis (Wet Analysis)

The particle size distribution for the micronized glycopyrrolate formulations was determined by Malvern Mastersizer 3000 using the Hydro MV wet dispersion unit as follows: the dispersion unit was filled with iso-octane (2,2,4-trimethylpentane). The pump speed was set to 3000 rpm. Ten millilitres of 0.1% lecithin in iso-octane was added to approximately 10 mg of the micronized glycopyrrolate formulation, this pre-dispersion was then sonicated for 3 minutes using a Sonopuls sonic probe at 50% intensity. The dispersed particles were added to the dispersion unit to reach an obscuration of 5-15%. The optical properties used included a refractive index of 1.52 and an absorption value of 1.0 for the glycopyrrolate, and a refractive index of 1.45 and an absorption value of 1.0 for the magnesium stearate and a refractive index of 1.391 for the iso-octane. Six replicates were performed per measurement.

Dynamic Vapour Sorption

The amorphous content for micronized glycopyrrolate was assessed by DVS using an SMS DVS Advantage instrument which was set to a temperature of 25° C. The humidity was increased from 0-90% RH then returned to 0% RH in steps of 10% RH, changes between steps which were triggered by a mass change of 0.0001 (% dm/dt).

Example 1

Formulation 1a (Jet Milled Glycopyrrolate Only in Dry Gas); Formulations 1b (Jet Milled Glycopyrrolate Only in Humidified Gas Using Liquid Aerosol; Formulations 1c (Co-Jet Milled Glycopyrrolate and Magnesium Stearate in Humidified Gas Using Liquid Aerosol)

Three separate glycopyrrolate formulations were made and analysed as follows:

Formulation 1a (Dry Milling Gas)

Unmicronised glycopyrrolate (15 g, $D_{10}$=20.6 µm, $D_{50}$=148.7 µm, $D_{90}$=409.7 µm determined by Malvern Mastersizer 3000 wet analysis method) was pre-stirred in a glass beaker using a metal spatula for 30 seconds before micronization in an AS-50 spiral jet mill (Inlet pressure=5 Bar, Grinding Pressure=3 Bar, Averaged Feed Rate=2 g/min). Formulation 1a was produced by using a dry milling gas having a humidity <20% RH (2.8-3.5% RH).

Formulations 1b (Humid Milling Gas Using Liquid Aerosol)

Formulation 1b was produced as above except that the humidity of the milling gas was elevated (31.6-36.2% RH and at 22° C.) using liquid aerosol. The outlet of an ultrasonic wave nebuliser was connected to the grinding chamber of an AS-50 jet mill via tube piping ensuring that water did not drip into the grinding chamber and that nebulised water aerosol combined with the unmicronised glycopyrrolate. The humidities were measured prior to jet milling by placing a portable hygrometer with the probe in the exiting gas stream at the outlet of the collection vessel.

Formulations 1c (Humid Milling Gas Using Liquid Aerosol and Magnesium Stearate)

Unmicronised glycopyrrolate (14.25 g, $D_{10}$=20.6 µm, $D_{50}$=148.7 µm, $D_{90}$=409.7 µm determined by Malvern Mastersizer 3000 wet analysis method) was pre-stirred with magnesium stearate (0.75 g, $D_{10}$=2.8 µm, $D_{50}$=8.8 µm, $D_{90}$=27.4 µm determined by Malvern Mastersizer 3000 wet analysis method) in a glass beaker using a metal spatula for 30 seconds before micronization in an AS-50 spiral jet mill (Inlet pressure=5 Bar, Grinding Pressure=3 Bar, Averaged Feed Rate=2 g/min). Formulation 1c was produced by using a milling gas at elevated humidity (32.4-37.1% RH and at 22° C.) using liquid aerosol. The outlet of an ultrasonic wave nebuliser was connected to the grinding chamber of an AS-50 jet mill via tube piping ensuring that water did not drip into the grinding chamber and that nebulised water aerosol combined with the unmicronised glycopyrrolate. The humidities were measured prior to jet milling by placing a portable hygrometer with the probe in the exiting gas stream at the outlet of the collection vessel.

Samples of the freshly micronized glycopyrrolate were immediately analysed using DVS, wet and dry particle size analysis.

Results: Formulation 1a-c

TABLE 1

Particle size (µm) distributions for Formulation 1a-c following wet analysis or dry analysis using the Malvern Mastersizer.

| Formulation | $D_{10}$ | | $D_{50}$ | | $D_{90}$ | |
|---|---|---|---|---|---|---|
| | Wet | Dry | Wet | Dry | Wet | Dry |
| 1a | 0.81 | 1.11 | 2.05 | 250 | 3.9 | 1340 |
| 1b | 1.38 | 0.355 | 4.06 | 2.74 | 9.08 | 9.17 |
| 1c | 1.7 | 2.12 | 12.8 | 41.3 | 224 | 267 |

Discussion: Formulations 1a-c

Figure 3:
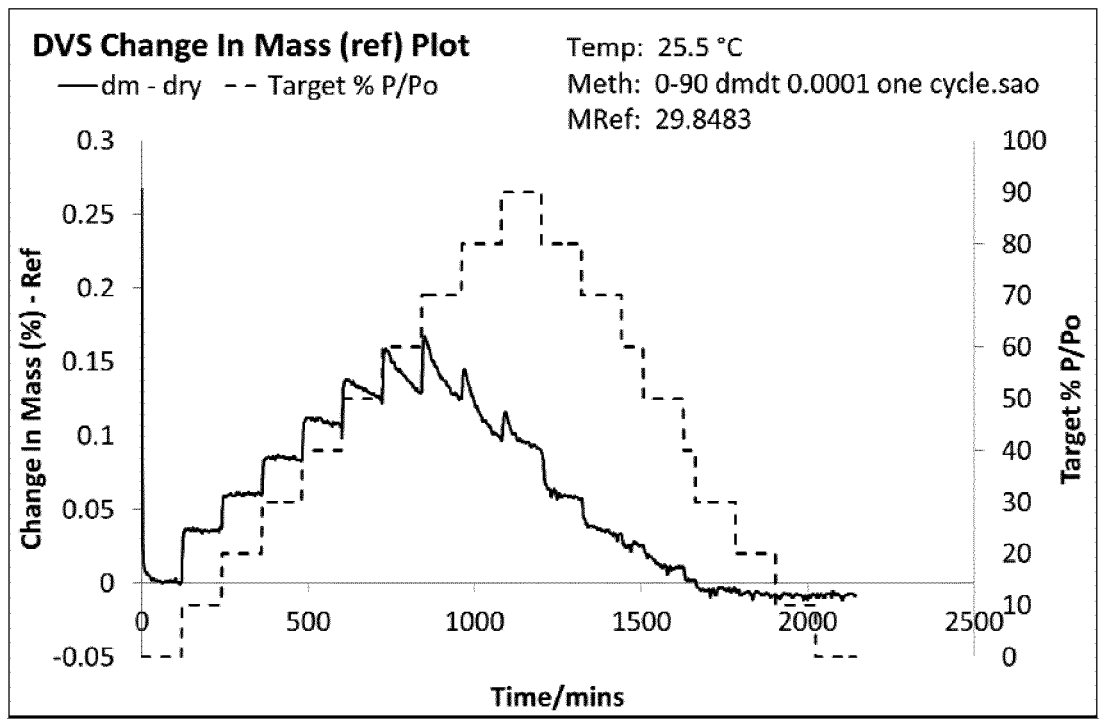
FIG. 3 shows the DVS trace for Formulation 1a, jet milled glycopyrrolate only using a milling gas having humidity <20% RH (2.8-3.5% RH) and the analysed immediately after micronisation.

When milled under dry conditions, freshly jet milled glycopyrrolate contains substantial amounts of amorphous material as confirmed by the DVS data for Formulation 1a (FIG. 3). The presence of this amorphous material in the company of moisture, if not controlled correctly, leads to the formation of large agglomerates in an unpredictable fashion. In the case of Formulation 1a, three separate samples were taken from jet milled powder and briefly transported in sealed scintillation vials for DVS, Wet PSD and Dry PSD analysis. First, the DVS analysis was started, followed by the Wet and Dry PSD analysis. Formulation 1a developed a significant amount of large agglomerates in the sealed scintillation vials prior to dry PSD analysis as shown by the $D_{90}$ and $D_{50}$ values (Table 1). The dry PSD analysis also demonstrates that Formulation 1a had equivalent $D_{10}$ values to the other Formulations 1b-c demonstrating that Formulation 1a still had a micronized component (Table 1). The wet PSD analysis shows that Formulation 1a had small PSD values (Table 1).

Figure 4:
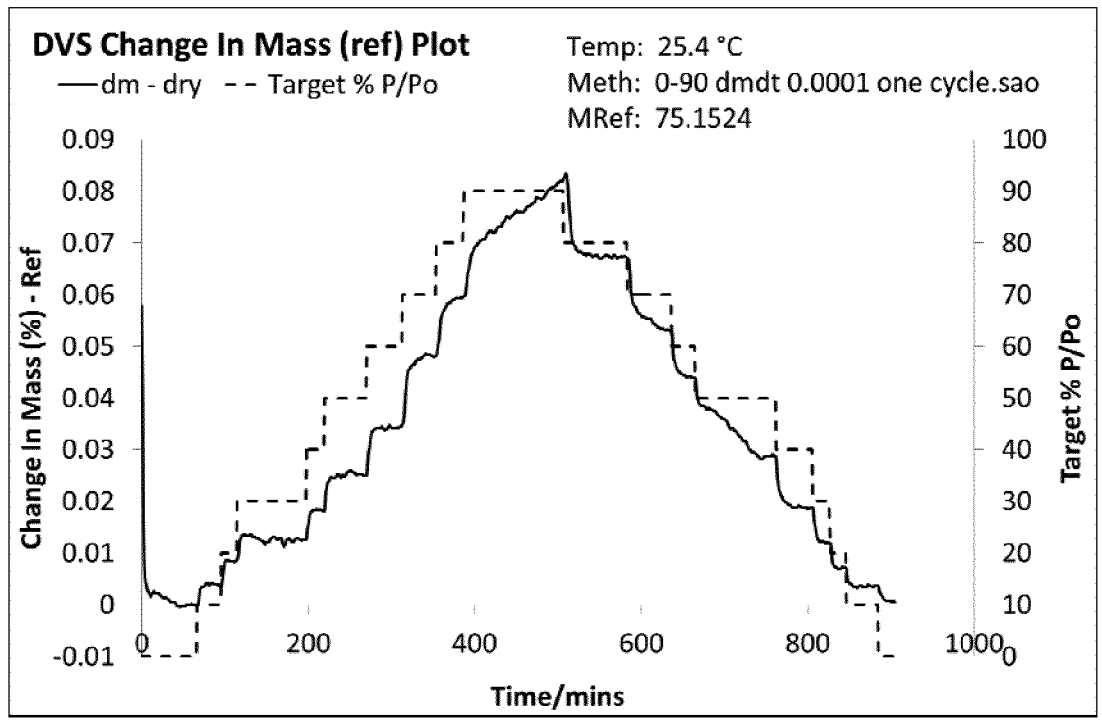
FIG. 4 shows the DVS trace for Formulation 1b, jet milled glycopyrrolate only using a milling gas having an elevated humidity (31.6-36.2% RH) and then analysed immediately after micronisation.

When jet milled with liquid aerosol in the grinding chamber, freshly jet milled glycopyrrolate formulations contain no amorphous material (Formulation 1b). The DVS trace demonstrates that no amorphous material was present in this freshly micronized glycopyrrolate (t=0) (see FIG. 4). Without this amorphous material on the surface of micronized glycopyrrolate, the particles do not form large agglomerates and remain respirable (i.e. $D_{50}$ less than 5 µm, see Table 1).

Figure 5:
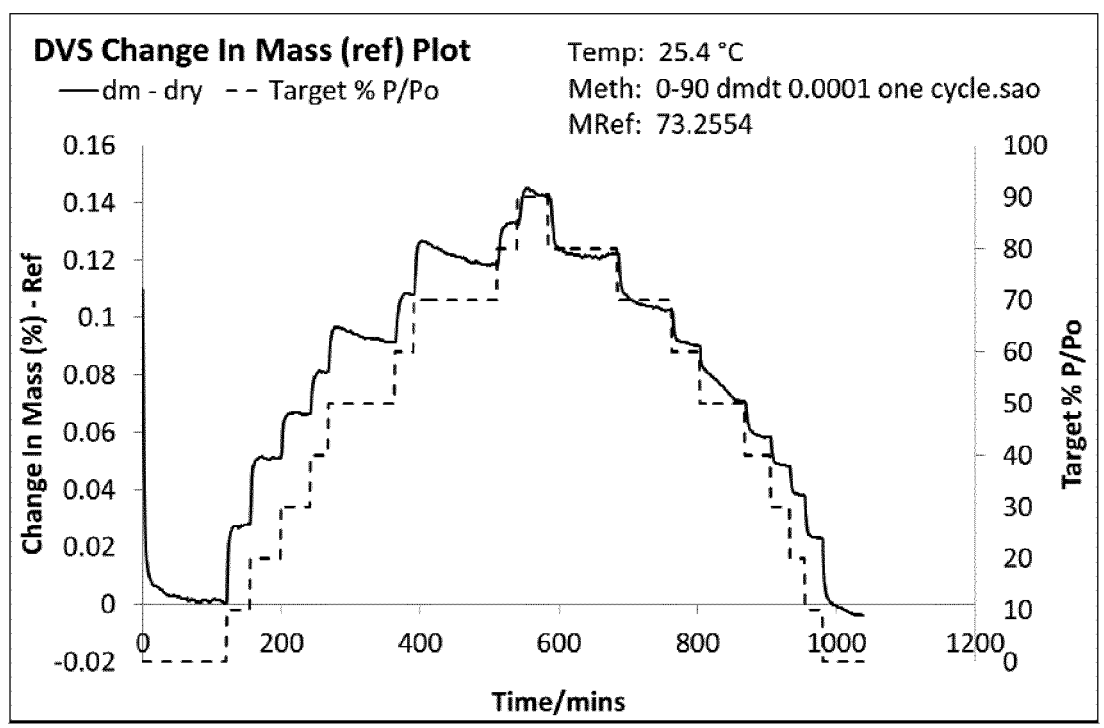
FIG. 5 shows the DVS trace for Formulation 1c, co-jet milled glycopyrrolate and magnesium stearate using a milling gas having an elevated humidity (32.4-37.1% RH) and then analysed immediately after co-micronisation.

Similarly, freshly co-jet milled glycopyrrolate and magnesium stearate formulations contain minimal amorphous material when co-jet milled under humid conditions (Formulation 1c), as is apparent from the DVS trace (FIG. 5). Without this amorphous material on the surface of micronized glycopyrrolate, the co-micronised particles do not form large agglomerates unlike Formulation 1a. The combination of the humidity and the magnesium stearate, however, reduces the milling efficiency resulting in an initial $D_{50}$ of 12.8 µm for Formulation 1c (see Table 1, Wet Analysis) compared to 2.05 µm and 4.06 µm (Wet Analysis for Formulations 1a and b respectively).

The invention claimed is:

1. A jet mill comprising a grinding chamber, an aerosol generator and a port, wherein the aerosol generator is located externally to the grinding chamber and is configured to supply a liquid aerosol into the grinding chamber via the port, wherein the port is configured to simultaneously supply a grinding material and the liquid aerosol into the grinding chamber.

2. The jet mill of claim 1, wherein the port is configured to supply a feed stock comprising a grinding material and the liquid aerosol into the grinding chamber.

3. The jet mill of claim 1, wherein the aerosol generator is configured to supply the liquid aerosol comprising droplets with a $D_{50}$ less than 100 µm prior to entering the grinding chamber as measured by laser diffraction.

4. The jet mill of claim 1, wherein the aerosol generator is configured to supply the liquid aerosol comprising droplets with a $D_{90}$ of less than 50 µm prior to entering the grinding chamber as measured by laser diffraction.

5. The jet mill of claim 1, wherein the aerosol generator is configured to supply the liquid aerosol comprising droplets with a $D_{90}$ of less than 20 µm prior to entering the grinding chamber as measured by laser diffraction.

6. The jet mill of claim 1, wherein the jet mill is selected from the group consisting of a spiral jet mill, a fluidized bed jet mill, an opposed fluid jet mill and a high density bed jet mill.

7. A method of producing micronized material, comprising:
jet milling a feed stock comprising a grinding material and a liquid aerosol in a jet mill, said jet mill comprising a grinding chamber, an aerosol generator and a port, wherein the aerosol generator is located externally to the grinding chamber and is configured to simultaneously supply the grinding material and the liquid aerosol into the grinding chamber.

8. The method of claim 7, wherein the grinding material comprises particulate material.

9. The method of claim 7, wherein the grinding material comprises a pharmaceutically active material.

10. The method of claim 7, wherein the grinding material comprises a pharmaceutical additive.

11. The method of claim 7, wherein the grinding material comprises a pharmaceutical excipient.

12. The method of claim 7, wherein a humidity in the grinding chamber is more than 10% RH as measured by a hygrometer, whereby the liquid aerosol imparts the humidity in the grinding chamber.

13. The method of claim 7, wherein the liquid aerosol comprises a pharmaceutically active material.

14. The method of claim 7, wherein the liquid aerosol comprises a pharmaceutical additive.

15. The method of claim 7, wherein the liquid aerosol comprises a pharmaceutical excipient.

16. The method of claim 7, wherein the grinding material comprises unmicronised particulate material.

17. The method of claim 7, wherein a humidity in the grinding chamber is more than 30% RH as measured by a hygrometer, whereby the liquid aerosol imparts the humidity in the grinding chamber.

* * * * *